(12) United States Patent
Audett et al.

(10) Patent No.: US 9,205,090 B2
(45) Date of Patent: *Dec. 8, 2015

(54) HIGH ENHANCER-LOADING POLYACRYLATE FORMULATION FOR TRANSDERMAL APPLICATIONS

(71) Applicant: ALZA Corporation, Vacaville, CA (US)

(72) Inventors: Jay Audett, Mountain View, CA (US); Jianye Wen, Palo Alto, CA (US); Eli J. Goldman, San Francisco, CA (US); Robert M. Gale, Los Altos, CA (US); Allison Luciano, Lebanon, NJ (US); Paul B. Foreman, Sommerville, NJ (US); Eric N. Silverberg, Summit, NJ (US)

(73) Assignee: ALZA Corporation, Vacaville, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 14/274,465

(22) Filed: May 9, 2014

(65) Prior Publication Data

US 2014/0249125 A1    Sep. 4, 2014

Related U.S. Application Data

(60) Continuation of application No. 13/776,452, filed on Feb. 25, 2013, now Pat. No. 8,758,808, which is a division of application No. 11/525,683, filed on Sep. 22, 2006, now Pat. No. 8,383,149.

(60) Provisional application No. 60/723,135, filed on Sep. 30, 2005, provisional application No. 60/720,201, filed on Sep. 23, 2005.

(51) Int. Cl.
| | |
|---|---|
| *A61K 9/70* | (2006.01) |
| *A61K 31/445* | (2006.01) |
| *A61K 31/4468* | (2006.01) |
| *A61F 13/02* | (2006.01) |
| *A61K 31/55* | (2006.01) |
| *A61K 47/32* | (2006.01) |
| *A61K 31/465* | (2006.01) |
| *C07D 401/04* | (2006.01) |
| *A61K 31/4439* | (2006.01) |
| *A61K 31/567* | (2006.01) |

(52) U.S. Cl.
CPC .............. *A61K 31/55* (2013.01); *A61K 9/7038* (2013.01); *A61K 9/7061* (2013.01); *A61K 31/4439* (2013.01); *A61K 31/465* (2013.01); *A61K 31/567* (2013.01); *A61K 47/32* (2013.01); *C07D 401/04* (2013.01)

(58) Field of Classification Search
None
See application file for complete search history.

(56) References Cited

U.S. PATENT DOCUMENTS

| | | |
|---|---|---|
| 3,532,708 A | 10/1970 | Blance |
| 3,558,574 A | 1/1971 | Doehnert |
| 3,598,122 A | 8/1971 | Zaffaroni |
| 3,598,123 A | 8/1971 | Zaffaroni |
| 4,286,592 A | 9/1981 | Chandrasekaran |
| 4,314,557 A | 2/1982 | Chandrasekaran |
| 4,322,516 A | 3/1982 | Wiest et al. |
| 4,379,454 A | 4/1983 | Campbell et al. |
| 4,466,953 A | 8/1984 | Kieth et al. |
| 4,470,962 A | 9/1984 | Kieth et al. |
| 4,554,324 A | 11/1985 | Husman et al. |
| 4,568,343 A | 2/1986 | Leeper et al. |
| 4,588,580 A | 5/1986 | Gale et al. |
| 4,597,961 A | 7/1986 | Etscorn |
| 4,608,249 A | 8/1986 | Otsuka et al. |
| 4,626,539 A | 12/1986 | Aungst et al. |
| 4,704,282 A | 11/1987 | Campbell et al. |
| 4,725,439 A | 2/1988 | Campbell et al. |
| 4,822,676 A | 4/1989 | Mudge |
| 4,839,174 A | 6/1989 | Baker et al. |
| 4,867,982 A | 9/1989 | Campbell et al. |
| 4,906,463 A | 3/1990 | Cleary et al. |
| 4,908,027 A | 3/1990 | Enscore et al. |
| 4,908,213 A | 3/1990 | Govil |
| 4,943,435 A | 7/1990 | Baker et al. |
| 4,954,343 A | 9/1990 | Hosaka et al. |

(Continued)

FOREIGN PATENT DOCUMENTS

| | | |
|---|---|---|
| CA | 2366862 | 9/2000 |
| EP | 0225005 | 6/1987 |

(Continued)

OTHER PUBLICATIONS

Yu, et al. "Transdermal Fentanyl Matrix Patch: Evaluation of a Parallel Binary Matrix System," Abstracts of the Millenial World Congress of Pharmaceutical Sciences, Moscone Center, San Francisco, California (Apr. 16-20, 2000); p. 69 [3-2169].

(Continued)

*Primary Examiner* — Kevin S Orwig

(74) *Attorney, Agent, or Firm* — Stoel Rives LLP; Zhi-Xiang (Alex) Oh

(57) ABSTRACT

A polyacrylate formulation suitable for delivery of drug to through a body surface of an individual. By loading the drug and permeation enhancers at a high concentration into a polyacrylate proadhesive that has inadequate adhesive properties for typical adhesive application on the skin, a formulation with desirable adhesive characteristics and effective therapeutic properties can be made. The proadhesive has higher glass transition temperature than typical pressure sensitive adhesives.

20 Claims, 1 Drawing Sheet

(56) References Cited

U.S. PATENT DOCUMENTS

| | | | |
|---|---|---|---|
| 5,004,610 A | 4/1991 | Osborne et al. |
| 5,006,342 A | 4/1991 | Cleary et al. |
| 5,077,104 A | 12/1991 | Hunt et al. |
| 5,135,753 A | 8/1992 | Baker et al. |
| 5,152,997 A | 10/1992 | Ebert et al. |
| 5,164,190 A | 11/1992 | Patel et al. |
| 5,186,939 A | 2/1993 | Cleary et al. |
| 5,230,896 A | 7/1993 | Yeh et al. |
| 5,310,559 A | 5/1994 | Shah et al. |
| 5,342,623 A | 8/1994 | Enscore et al. |
| 5,344,656 A | 9/1994 | Enscore et al. |
| 5,364,630 A | 11/1994 | Osborne et al. |
| 5,462,745 A | 10/1995 | Enscore et al. |
| 5,474,783 A | 12/1995 | Miranda et al. |
| 5,508,038 A | 4/1996 | Wang et al. |
| 5,573,778 A | 11/1996 | Therriault et al. |
| 5,613,958 A | 3/1997 | Kochinke et al. |
| 5,618,899 A | 4/1997 | Appelt et al. |
| 5,633,008 A | 5/1997 | Osborne et al. |
| 5,656,286 A | 8/1997 | Miranda et al. |
| 5,693,335 A | 12/1997 | Xia et al. |
| 5,730,999 A | 3/1998 | Lehmann et al. |
| 5,750,137 A | 5/1998 | Crisologo et al. |
| 5,762,952 A | 6/1998 | Barnhart et al. |
| 5,785,991 A | 7/1998 | Burkoth et al. |
| 5,843,468 A | 12/1998 | Burkoth et al. |
| 5,882,676 A | 3/1999 | Lee et al. |
| 5,948,433 A | 9/1999 | Burton et al. |
| 5,958,446 A | 9/1999 | Miranda et al. |
| 5,985,317 A | 11/1999 | Venkateshwaran et al. |
| 5,993,849 A | 11/1999 | Assmus et al. |
| 6,004,578 A | 12/1999 | Lee et al. |
| 6,024,976 A | 2/2000 | Miranda et al. |
| 6,063,399 A | 5/2000 | Assmus et al. |
| 6,077,527 A | 6/2000 | Tan et al. |
| 6,139,866 A | 10/2000 | Chono et al. |
| 6,165,497 A | 12/2000 | Osborne et al. |
| 6,203,817 B1 | 3/2001 | Cormier et al. |
| 6,231,885 B1 | 5/2001 | Carrara |
| 6,246,904 B1 | 6/2001 | Murdock |
| 6,512,010 B1 | 1/2003 | Gale et al. |
| 6,558,790 B1 | 5/2003 | Holguin et al. |
| 6,791,003 B1 | 9/2004 | Choi et al. |
| 7,622,136 B2 | 11/2009 | Gale |
| 7,645,813 B2 | 1/2010 | Kohara et al. |
| 8,383,149 B2 | 2/2013 | Audett et al. |
| 8,758,808 B2 | 6/2014 | Audett et al. |
| 9,056,061 B2 | 6/2015 | Gale et al. |
| 2002/0119187 A1 | 8/2002 | Cantor et al. |
| 2003/0002682 A1 | 1/2003 | Smith et al. |
| 2004/0001882 A1 | 1/2004 | Tisa-Bostedt et al. |
| 2004/0234582 A1 | 11/2004 | Kohara |
| 2004/0234584 A1 | 11/2004 | Muller et al. |
| 2004/0234585 A1 | 11/2004 | Gale |
| 2005/0048104 A1 | 3/2005 | Venkatraman et al. |
| 2007/0082038 A1 | 4/2007 | Gale et al. |
| 2007/0098771 A1 | 5/2007 | Audett et al. |
| 2013/0172428 A1 | 7/2013 | Audett et al. |

FOREIGN PATENT DOCUMENTS

| | | |
|---|---|---|
| EP | 0483105 | 6/1995 |
| EP | 0887075 | 12/1998 |
| EP | 078122 | 7/2000 |
| EP | 0842662 | 7/2002 |
| EP | 0591432 | 9/2002 |
| EP | 0617972 | 7/2003 |
| EP | 1369112 | 12/2003 |
| EP | 1201233 | 12/2004 |
| EP | 1639999 | 3/2006 |
| WO | WO 89/10108 | 11/1989 |
| WO | WO 95/18603 | 7/1995 |
| WO | WO 96/08229 | 3/1996 |
| WO | WO 00/24386 | 5/2000 |
| WO | WO 00/41538 | 7/2000 |
| WO | WO 00/44846 | 8/2000 |
| WO | WO 00/56290 | 9/2000 |
| WO | WO 01/26705 | 4/2001 |
| WO | WO 02/24157 | 3/2002 |
| WO | WO 02/26217 | 4/2002 |
| WO | WO 02/087482 | 11/2002 |
| WO | WO 03/070191 | 8/2003 |
| WO | WO 2007/035939 | 3/2007 |

OTHER PUBLICATIONS

Yoon, et al. "Transdermal Fentanyl Matrix Patch—Evaluation of a Parallel Binary Matrix System," Samyang Corporation (2000); alleged to be a presentation poster from the Millennial World Congress of Pharmaceutical Sciences held in San Francisco, California.

Physicians' Desk Reference; Duragesic® (Fentanyl Transdermal System); pp. 1786-1789; 56th edition; 1999.

Roy, et al. "Controlled Transdermal Delivery of Fentanyl: Characterizations of Pressure-Sensitive Adhesives for matrix Patch Design," Journal of Pharmaceutical Sciences vol. 85, No. 5 (1996); pp. 491-495.

Satas, Donates; Acrylic Adhesives; Handbook of Pressure Sensitive Adhesive Technology; Second Edition; 1989; pp. 396-418; Van Nostrand Reinhold, New York, USA.

Notification of Transmittal of the International Search Report and the Written Opinion of the International Searching Authority issued Apr. 17, 2007 in PCT Application No. PCT/US2006/037341.

Notification of Transmittal of the International Preliminary Report on Patentability issued Mar. 26, 2008 in International Application No. PCT/US2006/037341.

First Office Action issued Apr. 13, 2010 in U.S. Appl. No. 11/525,977.

Response to Apr. 13, 2010 Office Action filed Jul. 13, 2010 in U.S. Appl. No. 11/525,977.

Second Office Action issued Oct. 4, 2010 in U.S. Appl. No. 11/525,977.

Response to Oct. 4, 2010 Office Action filed Dec. 6, 2010 In U.S. Appl. No. 11/525,977.

Advisory Action issued Dec. 28, 2010 in U.S. Appl. No. 11/525,977.

Response to Dec. 28, 2010 Advisory Action filed Jan. 4, 2011 in U.S. Appl. No. 11/525,977.

Third Office Action issued Sep. 8, 2011 in U.S. Appl. No. 11/525,977.

Response to Sep. 8, 2001 Office Action filed Nov. 8, 2011 in U.S. Appl. No. 11/525,977.

Advisory Action issued Dec. 1, 2011 in U.S. Appl. No. 11/525,977.

Response to Dec. 1, 2011 Advisory Action filed Mar. 8, 2012 in U.S. Appl. No. 11/525,977.

First Office Action issued Nov. 17, 2009 in U.S. Appl. No. 11/525,683.

Response to Nov. 17, 2009 Office Action filed Feb. 17, 2010 in U.S. Appl. No. 11/525,683.

Second Office Action issued Jun. 10, 2010 in U.S. Appl. No. 11/525,683.

Response to Jun. 10, 2010 Office Action filed Oct. 11, 2010 in U.S. Appl. No. 11/525,683.

Third Office Action issued Dec. 22, 2010 in U.S. Appl. No. 11/525,683.

Response to Dec. 22, 2010 Office Action filed Feb. 18, 2011 in U.S. Appl. No. 11/525,683.

Advisory Action issued Mar. 7, 2011 in U.S. Appl. No. 11/525,683.

Response to Mar. 7, 2011 Advisory Action filed Jun. 22, 2011 in U.S. Appl. No. 11/525,683.

Fourth Office Action issue Jul. 14, 2011 in U.S. Appl. No. 11/525,683.

Examiner Interview Summary issued Aug. 29, 2011 in U.S. Appl. No. 11/525,683.

Appeal Brief filed Mar. 13, 2012 in U.S. Appl. No. 11/525,683.

Examiner Interview Summary issued Jun. 11, 2012 in U.S. Appl. No. 11/525,683.

Notice of Allowance and Fees Due issued Jun. 11, 2012 in U.S. Appl. No. 11/525,683.

(56) References Cited

OTHER PUBLICATIONS

Examiner Interview Summary issued Aug. 31, 2012 in U.S. Appl. No. 11/525,683.
EPO Communication issued Jan. 19, 2009 in European Application No. 06815388.1.
EPO Communication issued Jun. 21, 2010 in European Application No. 06815388.1.
EPO Communication issued Feb. 16, 2012 in European Application No. 06815388.1.
Response to EPO Communication filed Aug. 20, 2012 in European Application No. 06815388.1.
Summons to Attend Oral Proceedings issued Apr. 12, 2013 in corresponding European Application No. 06815388.1.
Extended European Search Report issued Sep. 7, 2011 in European Application No. 11152742.0.
Response to Sep. 7, 2011 EP Search Report filed Jul. 25, 2012 in European Application No. 11152742.0.
EPO Communication issued Apr. 11, 2013 in European Application No. 11152742.0.
"Nicotine Tartrate." IPCS Inchem Home. (http://inchem.org/documents/issc/icsc/eics0521.htm, accessed Mar. 30, 2010).
Office Action issued Sep. 11, 2013 in U.S. Appl. No. 11/525,977.
Response to Sep. 11, 2013 Non-Final Office Action filed Oct. 17, 2013 in U.S. Appl. No. 11/525,977.
Notice of Allowance issued Dec. 5, 2013 in U.S. Appl. No. 11/525,977.
Notice of Allowance issued Oct. 24, 2012 in U.S. Appl. No. 11/525,683.
Response to EPO Communication filed Jul. 28, 2009 in European Application No. 06815388.1.
Response to EPO Communication filed Jan. 31, 2011 in European Application No. 06815388.1.
Written Submissions in Response to Summons to Attend Oral Proceedings filed on Aug. 23, 2013 in European Application No. 06815388.1.
Written Submissions in Response to Summons to Attend Oral Proceedings filed on Aug. 30, 2013 in European Application No. 06815388.1.
Response to EPO Communication filed Oct. 18, 2013 in European Application No. 11152742.0.
Preliminary Amendment filed Feb. 25, 2013 in U.S. Appl. No. 13/776,452.
Notice of Allowance issued Oct. 21, 2013 in U.S. Appl. No. 13/776,452.
Notice of Allowance issued Feb. 19, 2014 in U.S. Appl. No. 13/776,452.

HIGH ENHANCER-LOADING POLYACRYLATE FORMULATION FOR TRANSDERMAL APPLICATIONS

CROSS REFERENCE TO RELATED U.S. APPLICATION DATA

This application is a continuation of U.S. application Ser. No. 13/776,452, filed Feb. 25, 2013, which is a divisional of U.S. application Ser. No. 11/525,683, filed on Sep. 22, 2006, which claims the benefit of U.S. Provisional Application No. 60/720,201, filed Sep. 23, 2005 and U.S. Provisional Application No. 60/723,135, filed Sep. 30, 2005. This application hereby incorporates by reference the U.S. applications and provisional applications enumerated herein.

TECHNICAL FIELD

This invention relates to transdermal drug delivery using a formulation having a polyacrylate. In particular, the invention relates to adhesive systems with polyacrylate having high enhancer and drug tolerance when used in transdermal drug delivery.

BACKGROUND

Transdermal devices for the delivery of biologically active agents have been used for maintaining health and therapeutically treating a wide variety of ailments. For example, analgesics, steroids, etc., have been delivered with such devices. Such transdermal devices include patches in which a biologically active agent is delivered to the body tissue passively without use of an additional energy source. Many such devices have been described, for example, in U.S. Pat. Nos. 3,598,122, 3,598,123, 4,379,454, 4,286,592, 4,314,557, 4,568,343, and U.S. Application No. 2003002682, all of which are incorporated herein by reference.

A transdermal patch is typically a small adhesive bandage that contains the drug to be delivered. A simple type of such transdermal patches is an adhesive monolith including a drug-containing reservoir disposed on a backing. The reservoir is typically formed from a pharmaceutically acceptable pressure sensitive adhesive. In some cases, the reservoir can be formed from a non-adhesive material, the skin-contacting surface of which is provided with a thin layer of a suitable adhesive. The rate at which the drug is administered to the patient from these patches can vary due to normal person-to-person and skin site-to-skin site variations in the permeability of skin to the drug.

Sometimes patches can be multilaminate or can include a liquid reservoir layer in the patches. A drug release-rate controlling membrane can be disposed between the drug reservoir and the skin-contacting adhesive. This membrane, by decreasing the release rate of drug from the patch, serves to reduce the effects of variations in skin permeability.

Although the transdermal delivery of therapeutic agents has been the subject of intense research and development for over 30 years, only a relatively small number of drug molecules are suitable for transdermal delivery due to the fact that human skin is an excellent barrier. Various techniques have been explored to enhance the permeation of drug molecules that are not otherwise suitable for transdermal delivery. Of these techniques, chemical enhancement is the most established and is currently employed commercially. Pressure sensitive adhesives, such as acrylic adhesives, are used in most transdermal drug delivery devices as a means of providing intimate contact between the drug delivery device and the skin. The use of enhancers, especially at high concentrations, usually has a significant impact on the properties of pressure sensitive adhesives, such as cohesive strength, adhesive flow, tackiness and adhesion strength. Therefore, pressure sensitive adhesives have to be designed in a way that they can provide the needed performance in the presence of enhancer.

Many systems with adhesives and permeation enhancers have been described in the past, e.g., U.S. Pat. Nos. 3,558, 574; 4,554,324; 4,822,676; 5,573,778, and 6,077,527. Some discussed the use of grafting macromers to the backbone (U.S. Pat. No. 5,573,778). Some discussed cross-linking (U.S. Pat. No. 6,077,527). However, at the present, there does not seem to be systems that have high enhancer and drug tolerance and yet provides pressure sensitive adhesive property.

There continues to be a need for improved transdermal systems, especially transdermal systems that can deliver pharmaceutical agents with a high load of pharmaceutical agents and/or permeation enhancers and yet provide desirable pressure sensitive property.

SUMMARY

The present invention provides a method and a device for transdermal delivery of biologically active agent or agents for therapeutic effects, especially delivery of the biologically active agents to a subject through skin or other body surface that is accessible from exterior without using endoscopic devices. An individual can wear the device over an extended period of time.

In one aspect, the present invention provides a transdermal system having improved enhancer loading, little or no cold flow, with desirable tack and adhesion.

In another aspect, the present invention relates to a transdermal system in which pharmaceutical properties, in particular, enhancer tolerance, is optimized by controlling the rheological properties of the polyacrylate material.

In one aspect of the invention, a novel technique is provided for increasing adhesive enhancer tolerance. Specifically, it has been discovered that by increasing the glass transition temperature of the acrylate polymer using the ratio of soft monomer and hard monomer, it is possible to load enhancer concentrations into the polymer at a high weight percent to obtain a formulation and still achieve desirable adhesive characteristics. It is possible to load drug and/or enhancer into the polymer composition to a high concentration, e.g., at greater than 20 dry weight %, greater than 30 dry weight % (or solids wt %), even up to 40-50 wt %, without adversely impacting the adhesion and rheological characteristics for pressure sensitive adhesive (PSA) application. With sufficient loadings of permeation enhancers in such formulations, sustained high rates of drug delivery can be achieved. With adequate adhesive properties, the resulting reservoir with sufficient drug loading and permeation enhancers can be used for effective therapeutic results. Prior to incorporation of drugs and ingredients, the polymeric materials are not suitable PSAs "as is" because of the stiffness of the polymer and insufficient adhesiveness or tackiness. These polymeric materials become adhesive and have the desired PSA characteristics after incorporating drug, permeation enhancer and optionally other ingredients in suitable quantities. Such polymeric materials, which are not suitable as a PSA as is (prior to incorporation of drugs and ingredients) but will have the desired PSA characteristics after incorporating drugs and/or other ingredients, can be called "proadhesive" herein.

In one aspect, the transdermal drug delivery device of the present invention has a reservoir including at least one drug, permeation enhancer and an acrylate polymer, wherein the acrylate polymer has no more than 60 wt % soft monomer, has at least 40 wt % hard monomer and 10 to 35 wt % polar functional monomer, the acrylate polymer constituting 45 wt % to 80 wt % of the reservoir. The acrylate polymer can have dissolved in it at least 30 wt % of the drug and permeation enhancer combination. The acrylate polymer has a $T_g$ of greater than −15° C. if without permeation enhancer and without drug. With drug and enhancers dissolved therein, the reservoir has pressure sensitive adhesive properties applicable to the body surface for transdermal delivery.

In another aspect, the present invention provides methods of making and using such transdermal drug delivery devices.

DETAILED DESCRIPTION

Figure 1:
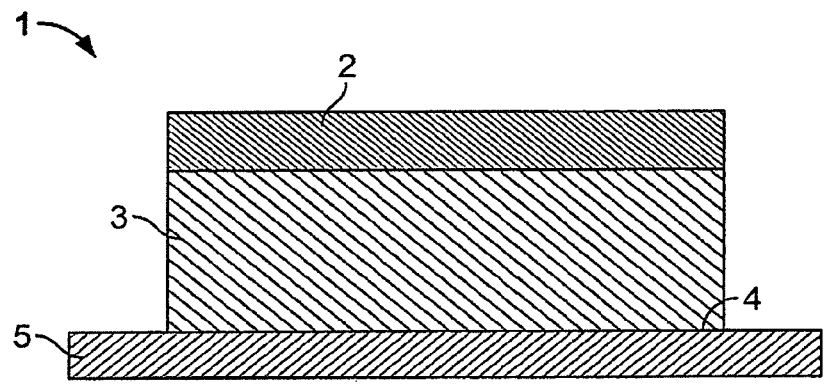
FIG. 1 illustrates a cross-section through a schematic, perspective view of one embodiment of a transdermal therapeutic system according to the present invention.

The present invention relates to transdermal delivery of pharmaceutical agents to a patient in need thereof involving the use of an acrylate polymer material that after incorporating drug(s) and other ingredients therein can act as a pressure sensitive adhesive (PSA) and maintain the transdermal delivery system on a body surface of an individual.

A pressure sensitive adhesive (PSA) is a material that adheres with light pressure, is aggressively and permanently tacky, exerts a strong holding force, and should be removable without leaving a residue. Pressure sensitive tack is the property that enables an adhesive to form a bond with the surface of another material upon brief contact under light pressure (usually no more than applied finger pressure). To achieve pressure sensitive tack, adhesives have to be easily deformed at the time scale allowed for bond formation, usually on the order of a fraction of a second. Besides tack, cohesive strength is desirable in transdermal uses to reduce the mass transfer of adhesive to the skin when the patch is removed. Resistance to cold flow is also desirable to prevent the adhesive from oozing from the patch during storage and use. It was found that the glass transition temperature, creep compliance (J), and elastic modulus (G') at the application temperature are important requirements for pressure sensitive adhesive performance.

Traditionally a transdermal drug delivery system was formulated with a pressure sensitive adhesive that has a glass transition temperature ($T_g$) in the range of −40° C. to −10° C. According to the present invention, the starting acrylate polymeric material (which can be formulated into an adhesive material having pharmaceuticals (or drugs) and/or enhancers) preferably has a glass transition temperature ($T_g$) in the range of about −15° C. or higher, more preferably −15° C. to 0° C., and even more preferably −10° C. to 0° C.; creep compliance of about $7 \times 10^{-5}$ cm$^2$/dyn (at 3600 second) or below, and modulus G' of about $8 \times 10^5$ dyn/cm$^2$ or above. The polymeric material can be formulated into a transdermal reservoir matrix (including carrier structure) with a combined drug and/or enhancer concentration greater than 30 dry weight percent (wt %), or even greater than 40 dry weight percent. The resulting transdermal adhesive formulation with drug agent(s) and/or enhancers will provide excellent adhesion with no cold flow, i.e., with no cold flow of an amount that is noticeable and would affect the normal use of the delivery system. By contrast, the starting proadhesive acrylate polymer has poor adhesive properties because the glass transition temperature is too high. Once plasticized in the transdermal formulation, the glass temperature drops into the pressure sensitive range, about −10 to −40° C., and the resulting creep compliance and storage modulus enables the achievement of good tack, with little or no cold flow. Creep compliance is an important parameter to evaluate cold flow behavior of a pressure sensitive adhesive (PSA). In a transdermal drug delivery system, if the creep compliance is large, the adhesive will have cold flow with time, i.e., the adhesive may loose its shape just because of the weight of the material in the device under gravity.

In describing the present invention, the following terms will be employed, and are intended to be defined as indicated below. As used in this specification and the appended claims, the singular forms "a," "an" and "the" include plural references unless the text content clearly dictates otherwise.

As used herein, the term "transdermal" refers to the use of skin, mucosa, and/or other body surfaces as a portal for the administration of drugs by topical application of the drug thereto for passage into the systemic circulation.

"Biologically active agent" is to be construed in its broadest sense to mean any material that is intended to produce some biological, beneficial, therapeutic, or other intended effect, such as enhancing permeation, relief of pain and contraception. As used herein, the term "drug" refers to any material that is intended to produce some biological, beneficial, therapeutic, or other intended effect, such as relief of symptoms of health disorder, but not agents (such as permeation enhancers) the primary effect of which is to aid in the delivery of another biologically active agent such as the therapeutic agent transdermally.

As used herein, the term "therapeutically effective" refers to the amount of drug or the rate of drug administration needed to produce the desired therapeutic result. As used herein, the term "permeation enhancement" intends an increase in the permeability of skin to a drug in the presence of a permeation enhancer as compared to permeability of skin to the drug in the absence of a permeation enhancer. A "permeation-enhancing amount" of a permeation-enhancer is an amount of the permeation enhancer sufficient to increase the permeability of the body surface of the drug to deliver the drug at a therapeutically effective rate.

"Acrylate", "polyacrylate" or "acrylic polymer", when referring to a polymer for an adhesive or proadhesive, refers to polymer or copolymer of acrylic acid, ester(s) thereof, acrylamide, or acrylonitrile. Unless specified otherwise, it can be a homopolymer, copolymer, or a blend of homopolymers and/or copolymers.

As used in the present invention, "soft" monomers refer to the monomers that have a $T_g$ of about −80 to −10° C. after polymerization into homopolymer; "hard" monomers refer to the monomers that have a $T_g$ of about 0 to 250° C. after forming homopolymer; and "functional" monomers refer to the monomers that contain hydrogen bonding functional groups such as hydroxyl, carboxyl or amino groups (e.g., alcohols, carboxylic acid, or amines), these polar groups tend to increase the hydrophilicity of the acrylate polymer and increase polar drug solubility.

Figure 2:
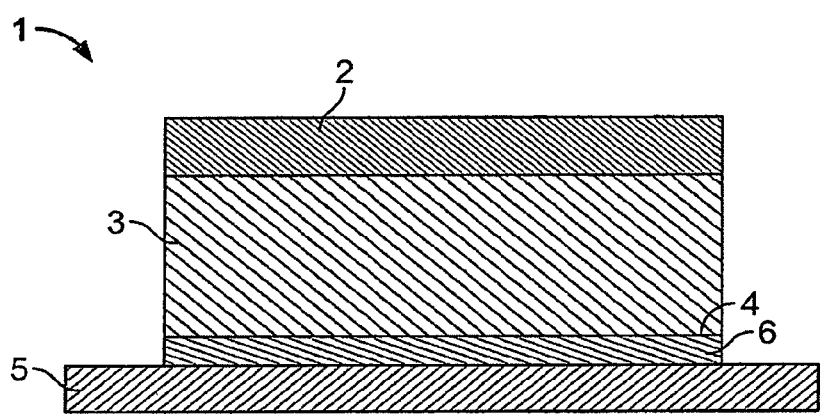
FIG. 2 illustrates a cross-section view through another embodiment of a transdermal therapeutic system of this invention.

Exemplary transdermal drug delivery systems of the present invention are illustrated by the embodiments shown in FIGS. 1 and 2. As shown in FIGS. 1 and 2, an embodiment of the transdermal monolithic patch 1 according to this invention has a backing layer 2, a drug reservoir 3 disposed on the backing layer 2, and a peelable protective layer 5. In the reservoir 3, which can be a layer, at least the skin-contacting surface 4 is an adhesive. The reservoir is a matrix (carrier) that is suitable for carrying the pharmaceutical agent (or drug) for transdermal delivery. Preferably, the whole matrix, with drugs and other optional ingredients, is a material that has the desired adhesive properties. The reservoir 3 can be either a single phase polymeric composition or a multiple phase polymeric composition. In a single phase polymeric composition the drug and all other components are present at concentrations no greater than, and preferably less than, their saturation concentrations in the reservoir 3. This produces a composition in which all components are dissolved. The reservoir 3 is formed using a pharmaceutically acceptable polymeric material that can provide acceptable adhesion for application to the body surface. In a multiple phase polymeric composition, at least one component, for example, a therapeutic drug, is present in amount more than the saturation concentration. In some embodiments, more than one component, e.g., a drug and a permeation enhancer, is present in amounts above saturation concentration. In the embodiment shown in FIG. 1, the adhesive acts as the reservoir and includes a drug.

In the embodiment shown in FIG. 2, the reservoir 3 is formed from a material that does not have adequate adhesive properties if without drug or permeation enhancer. In this embodiment of a monolithic patch 1, the skin-contacting surface of the reservoir 4 may be formulated with a thin adhesive coating 6. The reservoir 3 may be a single phase polymeric composition or a multiple phase polymeric composition as described earlier, except that it may not contain an adhesive with adequate adhesive bonding property for skin. The adhesive coating can contain the drug and permeation enhancer, as well as other ingredients.

The backing layer 2 may be formed from any material suitable for making transdermal delivery patches, such as a breathable or occlusive material including fabric or sheet, made of polyvinyl acetate, polyvinylidene chloride, polyethylene, polyurethane, polyester, ethylene vinyl acetate (EVA), polyethylene terephthalate, polybutylene terephthalate, coated paper products, aluminum sheet and the like, or a combination thereof. In preferred embodiments, the backing layer includes low density polyethylene (LDPE) materials, medium density polyethylene (MDPE) materials or high density polyethylene (HDPE) materials, e.g., SARANEX (Dow Chemical, Midland, Mich.). The backing layer may be a monolithic or a multilaminate layer. In preferred embodiments, the backing layer is a multilaminate layer including nonlinear LDPE layer/linear LDPE layer/nonlinear LDPE layer. The backing layer can have a thickness of about 0.012 mm (0.5 mil) to 0.125 mm (5 mil); preferably about 0.025 mm (1 mil) to 0.1 mm (4 mil); more preferably about 0.0625 mm (1.5 mil) to 0.0875 mm (3.5 mil).

The drug reservoir 3 is disposed on the backing layer 2. At least the skin-contacting surface of the reservoir is adhesive. As mentioned, the skin-contacting surface can have the structure of a layer of adhesive. The reservoir 3 may be formed from drug (or biological active agent) reservoir materials as known in the art. For example, the drug reservoir is formed from a polymeric material in which the drug has reasonable solubility for the drug to be delivered within the desired range, such as, a polyurethane, ethylene/vinyl acetate copolymer (EVA), acrylate, styrenic block copolymer, and the like. In preferred embodiments, the reservoir 3 is formed from a pharmaceutically acceptable adhesive or proadhesive, preferably acrylate copolymer-based, as described in greater detail below. The drug reservoir or the matrix layer can have a thickness of about 1-10 mils (0.025-0.25 mm), preferably about 2-5 mils (0.05-0.12 mm), more preferably about 2-3 mils (0.05-0.075 mm).

Preferred materials for making the adhesive reservoir or adhesive coating, and especially for making proadhesives according to the present invention include acrylates, which can be a copolymer of various monomers ((i) "soft" monomer, (ii) "hard" monomer, and optionally (iii) "functional" monomer) or blends including such copolymers. The acrylates (acrylic polymers) can be composed of a copolymer (e.g., a terpolymer) including at least two or more exemplary components selected from the group including acrylic acids, alkyl acrylates, methacrylates, copolymerizable secondary monomers or monomers with functional groups. Functional monomers are often used to adjust drug solubility, polymer cohesive strength, or polymer hydrophilicity. Examples of functional monomers are acids, e.g., acrylic acid, methacrylic acid and hydroxy-containing monomers such as hydroxyethyl acrylate, hydroxypropyl acrylate, acrylamides or methacrylamides that contain amino group and amino alcohols with amino group protected. Functional groups, such as acid and hydroxyl groups can also help to increase the solubility of basic ingredients (e.g., drugs) in the polymeric material. Additional useful "soft" and "hard" monomers include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers suitable in the practice of the invention are described in Satas, "Acrylic Adhesives," Handbook of pressure-Sensitive Adhesive Technology, 2nd ed., pp. 396-456 (D. Satas, ed.), Van Nostrand Reinhold, N.Y. (1989). Examples of acrylic adhesives are commercially available from National Starch and Chemical Company, Bridgewater, N.J.

The acrylate polymers can include cross-linked and non-cross-linked polymers. The polymers can be cross-linked by known methods to provide the desired polymers. However, cross-linking is hard to control and may result in polymeric materials that are too stiff or too soft. According to the present invention, it is preferred that the polymeric material for incorporation of drugs and other ingredients to be polymer without crosslinking and no cross-linking agent is used in forming the polymeric material. It is further preferred that the monomers do not self cross-link during polymerization. In the present invention, it was found that, instead of cross-linking to form a matrix adhesive with desired PSA properties for incorporating drugs and enhancers, good control of the PSA properties can be achieved by selecting polymeric materials that are too stiff prior to incorporation of drugs and other ingredients and subsequently incorporating such drugs and ingredients. It has been found that an acrylate polymer composition with a creep compliance (J) of $7 \times 10^{-5}$ cm$^2$/dyn or below and elastic modulus G' of $8 \times 10^5$ dyn/cm$^2$ or above, although too stiff as a PSA as is, after formulating with drug or enhancer or a combination thereof at a relative high concentration will achieve the desirable adhesive properties. The plasticizing or tackifying effect of the drug(s) and/or other ingredients on the polymeric material provides a means to achieve the desired adhesive properties in the reservoir.

Acrylate polymers, when the main monomer of which has the general formula $CH_2=CH-COOR$, are particularly useful as proadhesives. Typical main monomers are normally alkyl acrylates of 4 to 1 carbon atoms, preferably 4-10 carbons. Useful alkyl acrylates include ethyl acrylate, butyl acrylate, amyl acrylate, hexyl acrylate, 2-ethylhexyl acrylate, octyl acrylate, isooctyl acrylate, decyl acrylate, dodecyl acrylates, with 2-ethylhexyl acrylate, butyl acrylate, and iso-octyl acrylate being preferred. Such "soft" monomers if polymerized into homopolymer generally have a $T_g$ of less than about 0° C., preferably about −10° C. to −80° C., preferably about −20° C. to −80° C. Preferably, they are present in an amount of about 10 to 70 wt % (i.e., dry weight % or solids wt %), more preferably no more than about 60% by weight, more preferably no more than about 50 wt % of the total monomer weight and more preferably about 40 to 50 wt %. As used herein, when a monomer is said to be present in the acrylate polymer at a certain percentage, it is meant that the monomer has been polymerized in the acrylate polymer at that percentage of polymerization monomer ingredients.

"Hard" modifying monomers are mainly used to modify the adhesive properties, mainly glass transition temperature (e.g., to increase the $T_g$ and to make the resulting polymer stiffer at room temperature), to meet various application requirements. A hard monomer, if polymerized into homopolymer, has a $T_g$ of about 0 to 250° C., preferably about 20 to 250° C., more preferably in the range of about 30 to 150° C. (for convenience, this is referred to as the "homopolymer $T_g$" herein). The hard monomer component (or content in the polymer) is present in an amount of about 10 wt % or more, preferably in the range of about 30 to 60 wt %, preferably about 35 to 60 wt %, more preferably about 40 to 60 wt %, even more preferably about 40 to 50 wt % in the polymerization. Examples of hard modifying monomers are methyl acrylate, vinyl acetate, methyl methacrylate, isobutyl methacrylate, vinyl pyrrolidone, substituted acrylamides or methacrylamides. Homopolymers of these monomers generally have higher glass transition temperature than homopolymers of the soft monomers.

Certain nitrogen containing monomers can be included in the polymerization to raise the $T_g$. These include N-substituted acrylamides or methacrylamides, e.g., N-vinyl pyrrolidone, N-vinyl caprolactam, N-tertiary octyl acrylamide (t-octyl acrylamide), dimethyl acrylamide, diacetone acrylamide, N-tertiary butyl acrylamide (t-butyl acrylamide and N-isopropyl acrylamide (i-propyl acrylamide). Further examples of monomers that can be used in polymerization to modify and raise the $T_g$ of the polymer include cyanoethylacrylates, N-vinyl acetamide, N-vinyl formamide, glycidyl methacrylate and allyl glycidyl ether.

Functional monomers can be used to either provide needed functionality for solubilizing agents in the polyacrylate or improve cohesive properties. Examples of functional monomers are organic acids, e.g., acrylic acid, methacrylic acid, and hydroxyl-containing monomers such as hydroxyethyl acrylate. Preferred functional monomers when incorporated into the polymer result in acid groups, i.e., —COOH, hydroxyl groups, i.e., —OH, or amino groups in the polymer for affecting the solubility of basic agents such as basic drugs. Examples of hydroxy functional monomers include hydroxyethyl acrylate, hydroxypropyl acrylate, hydroxyethyl methacrylate and hydroxypropyl methacrylate. The hydroxyl groups can be primary, secondary or tertiary hydroxyl. In some cases, the acrylate polymer can includes at least one non-primary hydroxyl functional monomer component to provide orientation of the functional group in the polymer. Suitable non-primary hydroxyl functional monomers are secondary hydroxyl functional monomers such as hydroxypropyl acrylate. Useful carboxylic acid monomers to provide the functional group preferably contain from about 3 to about 6 carbon atoms and include, among others, acrylic acid, methacrylic acid, itaconic acid, and the like. Acrylic acid, methacrylic acid and mixtures thereof are particularly preferred as acids.

A functional monomer can also be a hard monomer, if its homopolymer has the high $T_g$. Such functional monomers that can also function as hard monomers include, e.g., hydroxyethyl acrylate, hydroxypropyl acrylate, acrylic acid, dimethylacrylamide, dimethylaminoethyl methacrylate, tert-butylaminoethyl methacrylate, methoxyethyl methacrylate, and the like.

The functional monomer(s) are preferably present in the acrylate polymer in an amount of about at least 5 wt %, preferably at least 10 wt %, preferably 10 to 40 wt %, more preferably about 10 to 30 wt %, more preferably about 10 to 20 wt %, even more preferably 10 to 15 wt %, even though some of the functional monomer(s) may be hard monomers. Examples of preferred functional monomer component include acrylic acid and hydroxyethyl acrylate, acrylamides or methacrylamides that contain amino group and amino alcohols with amino group protected. One of the applications of using functional monomers is to make a polar proadhesive having higher enhancer tolerance, in that, for example, the resulting PSA with the enhancers and/or drug will not phase separate or have excessive cold flow.

In certain embodiments, the hard monomer(s) that are not also functional monomer can constitute about 10 to 60 wt %, preferably about 40 to 60 wt % of the acrylate monomer, especially in cases in which no acidic functional hard monomer and less than about 20 wt % of hydroxyl functional hard monomer are included in the acrylate polymer. In other embodiments, the hard monomer(s) that are not also functional monomer can constitute about 5 to 15 wt %, e.g., about 10 wt % of the acrylate monomer, especially in cases in which a large amount (e.g., about 25 wt % or more) of functional hard monomer(s) are included, such as when more than about 5 wt % acidic hard functional monomers and 10 or more wt % (e.g., about 10-25 wt %) hydroxyl functional hard monomer(s) are included in the acrylate polymer.

Below is a table showing the $T_g$'s of exemplary soft and hard homopolymers the monomers of which are useful for making proadhesive of the present invention. Some of the monomers (e.g., acrylic acid, hydroxyethyl acrylate) are also functional monomers.

| | |
|---|---|
| poly(hydroxyethyl acrylate) (hard/functional monomer) | around 100° C. |
| poly(acrylic acid) (hard/functional monomer) | 106° C. |
| poly(vinyl acetate) (hard monomer) | 30° C. |
| poly(ethylhexyl acrylate) (soft monomer) | −70° C. |
| poly(isopropyl acrylate) (soft monomer) | −8° C. |
| poly(n-propyl acrylate) (soft monomer) | −52° C. |
| poly(isobutyl acrylate) (soft monomer) | −40° C. |
| poly(n-butyl acrylate) (soft monomer) | −54° C. |
| poly(n-octyl acrylate) (soft monomer) | −80° C. |

It has been found that the soft monomers 2-ethylhexyl acrylate and butyl acrylate are especially suitable to polymerize with functional monomers hydroxyethyl acrylate or acrylic acid either alone or in combination to form the acrylate polymer of the present invention. Further, the hard monomer vinyl acetate has been found to be very useful to polymerize with the soft monomers 2-ethylhexyl acrylate and butyl acrylate, either alone or in combination to form the proadhesive. Thus, the acrylate proadhesive polymer of the present invention is especially suitable to be made from 2-ethylhexyl acrylate or butyl acrylate copolymerized with hydroxyethyl acrylate, acrylic acid, or vinyl acetate, either alone or in combination. Another preferred hard monomer is t-octyl acrylamide, which can be used alone or in combination with other hard monomers such as acrylic acid and hydroxyethyl acrylate.

In an embodiment, the proadhesive is made by polymerizing monomers including about 30 to 75 wt % vinyl acetate, about 10-40 wt % hydroxyl functional monomer and about 10-70 wt % soft monomer such as 2-ethylhexyl acrylate or butyl acrylate. In a preferred embodiment, the proadhesive is made by polymerizing monomers including about 50 to 60 wt % vinyl acetate, about 10-20 wt % hydroxyethyl acrylate, and about 20-40 wt % 2-ethylhexyl acrylate. In some cases, no carboxyl (acid) group is used. Hydroxyethyl acrylate or hydroxypropyl acrylate can be used to provide hydroxyl functionality. For example, one embodiment is a proadhesive having about 50 wt % vinyl acetate, about 10 wt % hydroxyethyl acrylate, and about 40 wt % 2-ethylhexyl acrylate. As used herein, when a specific percentage is mentioned, it is contemplated there may be slight variations, e.g., of plus or minus 5% of the specific percentage (i.e., about 10 wt % may included 10 wt %±0.5 wt %). One other embodiment is a proadhesive having about 60 wt % vinyl acetate, about 20 wt % hydroxyethyl acrylate, and about 20 wt % 2-ethylhexyl acrylate.

In another embodiment, the proadhesive is made by polymerizing monomers including both monomer with hydroxyl group and monomer with carboxyl group. For example, certain preferred monomer combination for polymerization include an alkyl acrylate, an acrylamide, a monomer with hydroxyl group and a monomer with carboxyl group, e.g., making a proadhesive by polymerizing butyl acrylate, 2-hydroxyethyl acrylate or 2 hydroxypropyl acrylate or hydroxypropyl methacrylate, t-octyl acrylamide, and acrylic acid. In an embodiment, greater than 3 wt % of a hydroxypropyl acrylate or hydroxylpropyl methacrylate is used in making the acrylate polymer.

In certain cases for making a proadhesive in which both monomers with hydroxyl groups and monomer with carboxyl groups are to be polymerized with a soft monomer, e.g., butyl acrylate, the monomer proportions in the polymerization includes about 55 to 65 wt % soft monomer (e.g., butyl acrylate), about 5 to 15 wt % t-octyl acrylamide, about 20 to 30 wt % hydroxyethyl or hydroxypropyl acrylate and about 5 to 10 wt % acid monomer such as acrylic acid. In one embodiment, the acrylate polymer includes about 59 wt % butyl acrylate, about 10 wt % t-octyl acrylamide, about 25 wt % hydroxypropyl acrylate and about 6 wt % acrylic acid. In another embodiment, the hydroxypropyl acrylate is replaced with hydroxyethyl acrylate.

It is important that with the incorporation of a large amount of permeation enhancers, the $T_g$ of the resulting reservoir (with the drug, permeation enhancers and other ingredients) is such that the resulting reservoir would have good PSA properties for application to the body surface of an individual. Further, the resulting reservoir should not have cold flow that affects the normal application of the transdermal delivery. The acrylate polymer (or a blend of acrylate polymers) constitutes preferably about 40 wt % to 90 wt %, more preferably about 45 wt % to 80 wt % of the reservoir. It is possible to load drug and/or enhancer into the polymer composition to a high concentration. For example, the permeation enhancer, with or without drug, can be at or greater than about 20 dry weight %, preferably at or greater than about 30 dry weight % (or solids wt %), even more preferably up to about 40 to 50 wt % of the drug delivery reservoir, without adversely impacting the adhesion and rheological characteristics for pressure sensitive adhesive (PSA) application.

Preferred acrylate polymers or blends thereof provide the acrylic pressure sensitive properties in the delivery system glass transition temperature of about −10 to −40° C., preferably about −20 to −30° C. at application on a surface. The $T_g$ of an acrylate polymer can be determined by differential scanning calorimetry (DSC) known in the art. Also, theoretical ways of calculating the $T_g$ of acrylate polymers are also known. Thus, one having a sample of an acrylate polymer will be able to experimentally determine the $T_g$, for example, by DSC. One can also determine the monomer composition of the acrylate polymer and estimate theoretically the $T_g$ by calculation. From the knowledge of the monomer composition of an acrylate polymer having drugs and enhancers, one can also make the acrylate polymer without the drug and enhancer and determine the $T_g$. According to the present invention, the acrylate materials, before dissolving the drug(s), permeation enhancers, etc., have $T_g$'s that are in the range of about −20 to 10° C., and have rheological properties that are not quite suitable for use directly as a PSA to skin because of the stiffness of the material. The acrylate polymers preferably have a molecular weight in a range of about 200,000 to 600,000. Molecular weight of acrylate polymers can be measured by gel permeation chromatography, which is known to those skilled in the art.

To control the physical characteristics of the acrylate polymer and the polymerization, it is preferred that monomers of molecular weight of below 500, even more preferably below 200 be used in the polymerization. Further, although optionally larger molecular weight monomers (linear macromonomers such as ELVACITE™ from ICI) can be used in the polymerization, it is preferred that they are not used. Thus, preferably no monomer of molecular weight (MW) above 5000, more preferably no monomer of MW above 2000, even more preferably no monomer of MW above 500, is to be included in the polymerization to form the acrylate polymer. Thus, in the present invention, preferably, proadhesive polymers can be formed without macromonomers, or substantially without macromonomers, to have adhesive properties too stiff for PSA as is without incorporation of a large amount of permeation enhancers and drug. However, such proadhesives will become suitable for adhering to the skin as PSA in patch application after the appropriate amount of permeation enhancer and drug are dissolved therein.

However, if desired, in certain embodiments, optionally, the reservoir can include diluent materials capable of reducing quick tack, increasing viscosity, and/or toughening the reservoir structure, such as polybutylmethacrylate (ELVACITE, manufactured by ICI Acrylics, e.g., ELVACITE 1010, ELVACITE 1020, ELVACITE 20), polyvinylpyrrolidone, high molecular weight acrylates, i.e., acrylates having an average molecular weight of at least 500,000, and the like.

The acrylate polymers of the present invention can dissolve a large amount of permeation enhancer and allow the resulting drug and permeation enhancer-containing adhesive to have the desired adhesive and cohesive property without the drug or permeation enhancer separating out of the acrylate polymer matrix either as crystals or as oil. The resulting composition will be in the $T_g$ and compliance range that it can be applied to a body surface without leaving an undesirable amount of residue material on the body surface upon removal of the device. The preferred acrylate polymer is not cross-linked. It is contemplated, however, that if desired, a nonsubstantial amount of cross-linking may be done, so long as it does not change substantially the $T_g$, creep compliance and elastic modulus of the acrylate polymer. It is also found that higher $T_g$ and higher molecular weight of the acrylate are important for the acrylate polymer tolerating high enhancer loading. Since the measurement of the molecular weight of an acrylate polymer is difficult, precise or definite values are often not obtainable. More readily obtainable parameters that are related to molecular weight and drug and enhancer tolerance (i.e., solubility) are creep compliance and elastic modulus.

Enhancers typically behave as plasticizers to acrylate adhesives. The addition of an enhancer will result in a decrease in modulus as well as an increase in creep compliance, the effect of which is significant at high enhancer loading. A high loading of enhancers will also lower the $T_g$ of the acrylate polymer. Thus, to achieve a proadhesive that is tolerant of high enhancer loading, other than increasing the $T_g$ by using a higher ratio of hard monomer to soft monomer and the selection of suitable monomers, it is desirable to provide suitable higher molecular weight such that chain entanglement would help to achieve the desirable rheology. As a result, selecting a higher $T_g$ and higher molecular weight for a proadhesive will increase the elastic modulus and decrease the creep compliance of the acrylate, making the proadhesive more enhancer tolerant. The measurement of the molecular weight of an acrylate polymer is often method-dependant and is strongly affected by polymer composition, since acrylate polymers discussed here are mostly copolymers, not homopolymers. More readily obtainable parameters that relate to molecular weight and drug and enhancer tolerance (i.e., solubility) are creep compliance and elastic modulus.

According to the present invention, especially useful polymeric materials for forming drug-containing PSA are acrylate polymers that, before the incorporation of drugs, enhancers, etc., and other ingredients for transdermal formation, have creep compliance (measured at 30° C. and 3600 second) of about $7 \times 10^{-5}$ cm$^2$/dyn or below and storage modulus G' about $8 \times 10^5$ dyn/cm$^2$ or above. Preferably the creep compliance is about $6 \times 10^{-5}$ cm$^2$/dyn to $2 \times 10^{-6}$ cm$^2$/dyn, more preferably about $5 \times 10^{-5}$ cm$^2$/dyn to $4 \times 10^{-6}$ cm$^2$/dyn. Preferably the storage modulus is about $8 \times 10^5$ dyn/cm$^2$ to $5 \times 10^6$ dyn/cm$^2$, more preferably about $9 \times 10^5$ dyn/cm$^2$ to $3 \times 10^6$ dyn/cm$^2$. Such creep compliance and modulus will render these acrylate polymers too stiff and unsuitable "as is" for dermal PSA applications. However, it was found that after formulating into a transdermal system with drugs, permeation enhancers, and the like, which produce plasticizing effect as well as tackifying effect, the acrylate polymers plasticized with permeation enhancers and/or drug would have a desirable storage modulus and creep compliance that are suitable for transdermal PSA applications. For example, the plasticized material would have a resulting creep compliance that is about $1 \times 10^{-3}$ cm$^2$/dyn or less, preferably more than about $7 \times 10^{-5}$ cm$^2$/dyn, preferably from about $7 \times 10^{-5}$ cm$^2$/dyn to $6 \times 10^4$ cm$^2$/dyn, more preferably about $1 \times 10^4$ cm$^2$/dyn to $6 \times 10$ cm$^2$/dyn. The preferred storage modulus of the plasticized acrylate polymer is about $1 \times 10^5$ dyn/cm$^2$ to $8 \times 10^5$ dyn/cm$^2$, preferably about $1.2 \times 10^5$ dyn/cm$^2$ to $6 \times 10^5$ dyn/cm$^2$, more preferably about $1.4 \times 10^5$ dyn/cm$^2$ to $5 \times 10^5$ dyn/cm$^2$.

It was found that incorporating the proper selection of drug and other ingredients (such as permeation enhancers) and using the appropriate amounts thereof can change the $T_g$, storage modulus G' and creep compliance to result in an effective transdermal drug delivery system with the right adhesive properties for the desirable length of time, such as 24 hours, 3 day, or even 7 day application on a body surface. Such transdermal drug delivery systems will have little or no cold flow. As used herein, "little cold flow" means that any shape change of the device caused by cold flow is not noticeable by an average person on which the device is applied over the time of use. Particularly useful for forming adhesives incorporating an increased amount of beneficial agents (including drugs and permeation enhancers) over prior adhesives in transdermal drug delivery are the acrylic formulations containing a relatively lower percentage of soft monomers. It has been found that increasing the molecular weight increases the modulus of elasticity and decreases the polymer chain mobility via chain entanglements. Also, increasing hard monomer content increases the glass transition temperature.

As aforementioned, the reservoir 3 can include a single phase polymeric composition, free of undissolved components, containing an amount of the drug sufficient to induce and maintain the desired therapeutic effect in a human for, e.g., at least three days. The present invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antischizophrenia agents, antithyroid agents, antitussives, antiviral agents, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, norelgestromin, 5-hydroxytryptamine antagonists, drugs for the treatment of hyperlipoproteinemia, hypnotics and sedatives, immunosupressive agents, laxatives, methylxanthines, moncamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like, alone or in combination. Basic drugs such as opioids (e.g., fentanyl and analogs: alfentanil, carfentanil, lofentanil, remifentanil, sufentanil, trefentanil, and the like), galantamine, and the salts and esters of such basic drugs are well suited to be incorporated in the reservoir with the acrylate polymer.

The drug can be included in the reservoir at an amount of about 1 to 20 wt %, preferably about 2 to 15 wt %. With the aid of a large quantity of permeation enhancers in a reservoir of the present invention, many drugs can now be delivered through the body surface for therapeutic effect.

As indicated in the above, in some embodiments, the reservoir or the adhesive may contain additional components such as additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art. Typically, such materials are present below saturation concentration in the reservoir.

Permeation enhancers can be useful for increasing the skin permeability of the drug or drugs to achieve delivery at therapeutically effective rates. Such permeation enhancers can be applied to the skin by pretreatment or currently with the drug, for example, by incorporation in the reservoir. A permeation enhancer should have the ability to enhance the permeability of the skin for one, or more drugs or other biologically active agents. A useful permeation enhancer would enhance permeability of the desired drug or biologically active agent at a rate adequate to achieve therapeutic plasma concentrations from a reasonably sized patch (e.g., about 5 to 50 cm$^2$, although it may be larger). Some useful permeation enhancers include non-ionic surfactants, one or more can be selected from the group including glyceryl mono-oleate, glyceryl mono-laurate, sorbitan mono-oleate, glyceryl tri-oleate, and isopropyl myristate. The non-ionic surfactant can be used in the amount of about 0.1 to 30 wt % solids to the total composition of the reservoir layer. Examples of permeation enhancers include, but are not limited to, fatty acid esters of fatty acid esters of alcohols, including glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethy-1 lauramide; lauramide diethanolamine (DEA). Preferred enhancers include, but are not limited to, lauryl pyroglutamate (LP), glyceryl monolaurate (GML), glyceryl monocaprylate, glyceryl monocaprate, glyceryl monooleate (GMO), oleic acid, N-lauryl sarcosine, ethyl palmitate, laureth-2, laureth-4, and sorbitan monolaurate. Additional examples of suitable permeation enhancers are described, for example, in U.S. Pat. Nos. 5,785,991; 5,843,468; 5,882,676; and 6,004,578.

In some embodiments, especially some in which the reservoir does not necessarily have adequate adhesive properties and a separate adhesive layer is used, a dissolution assistant can be incorporated in the reservoir to increase the concentration of the drug or biologically active ingredient within the reservoir layer. As for the dissolution assistant, one or more can be selected from the group including triacetin, isopropyl alcohol, propylene glycol, dimethylacetamide, propylene carbonate, diethylethanolamine, diethyl amine, triethylarnine, N-methyl morpholine, benzalkonium chloride, oleic acid, lactic acid, adipic acid, succinic acid, glutaric acid, sebacic acid, and hydroxycaprilic acid. Permeation enhancers can also act as solubilization assistants.

As used herein, "permeation enhancers" is meant to include dissolution assistants, unless specified otherwise in context. Permeation enhancers (not including dissolution assistants) can constitute up to about 35% solids by weight, preferably about 0.1 to 30% by weight and more preferably about 1 to 25% by weight in the reservoir in a transdermal drug delivery device of the present invention. As used herein, the term "combination" when refers to selection of two or more chemicals means the chemicals are selected together and not necessarily that they be chemically combined together in a reaction.

In some embodiments, especially for drugs that do not transdermally permeate readily, a large amount of permeation enhancer may be needed to aid the drug in transdermal delivery. The present invention is especially suitable for such transdermal delivery systems. In such cases, one or more permeation enhancers, alone or in combination, and which may include dissolution assistants, can constitute about 5 to 40% by weight, preferably about 10 to 35% by weight, and more preferably about 15 to 30% by weight solids of the resulting reservoir that has adequate pressure sensitive adhesive properties.

In certain embodiments, optionally, certain other plasticizer or tackifying agent is incorporated in the polyacrylate composition to improve the adhesive characteristics. Examples of suitable tackifying agents include, but are not limited to, aliphatic hydrocarbons; aromatic hydrocarbons; hydrogenated esters; polyterpenes; hydrogenated wood resins; tackifying resins such as ESCOREZ, aliphatic hydrocarbon resins made from cationic polymerization of petrochemical feedstocks or the thermal polymerization and subsequent hydrogenation of petrochemical feedstocks, rosin ester tackifiers, and the like; mineral oil and combinations thereof. The tackifying agent employed should be compatible with the polymer or blend of polymers.

Transdermal delivery patches typically have protective layers. For example, as shown in FIGS. 1 and 2, the patch 1 further includes a peelable protective layer 5. The protective layer 5 is made of a polymeric material that may be optionally metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In preferred embodiments, the protective layer includes a siliconized polyester sheet.

A wide variety of materials that can be used for fabricating the various layers of the transdermal delivery patches according to this invention have been described above. It is contemplated that the use of materials other than those specifically disclosed herein, including those which may hereafter become known to the art to be capable of performing the necessary functions is practicable.

With patches made with acrylate polymers of the present invention, to assess transdermal flux of a drug from a patch, flux can be measured with a standard procedure using Franz cells or using an array of formulations. Flux experiments are done on isolated human cadaver epidermis. With Franz cells, in each Franz diffusion cell a disc of epidermis is placed on the receptor compartment. A transdermal delivery system is placed over the diffusion area (1.98 cm$^2$) in the center of the receptor. The donor compartment is then added and clamped to the assembly. At time 0, receptor medium solution (between 21 and 24 ml, exactly measured) is added into the receptor compartment and the cell maintained at 35° C. This temperature yields a skin surface temperature of 30-32° C. Samples of the receptor compartment are taken periodically to determine the skin flux and analyzed by HPLC. In testing flux with an array of transdermal miniature patches, formulations are prepared by mixing stock solutions of each of the mixture components of formulation in organic solvents (about 15 wt % solids), followed by a mixing process. The mixtures are then aliquoted onto arrays as 4-mm diameter drops and allowed to dry, leaving behind solid samples or "dots." (i.e., mini-patches). The miniature patches in the arrays are then tested individually for skin flux using a permeation array, whose principle of drug flux from a formulation patch through epidermis to a compartment of receptor medium is similar to that of Franz cells (an array of miniature cells). The test array has a plurality of cells, a piece of isolated human epidermis large enough to cover the whole array, and a multiple well plate with wells acting as the receptor compartments filled with receptor medium. The assembled permeation arrays are stored at 32° C. and 60% relative humidity for the duration of the permeation experiments. Receptor fluid is auto-sampled from each of the permeation wells at regular intervals and then measured by HPLC for flux of the drug.

Administration of the Drug

On application of the transdermal device (patch) to the skin of an individual in need thereof, the drug in the drug reservoir of the transdermal patch diffuses into the skin where it is absorbed into the bloodstream to produce a systemic therapeutic effect. The onset of the therapeutic depends on various factors, such as, potency of the drug, the solubility and diffusivity of the drug in the skin, thickness of the skin, concentration of the drug within the skin application site, concentration of the drug in the drug reservoir, and the like. Typically, it is preferable that a patient experiences an adequate effect within a few hours (e.g., 3-6 hours) of initial application. However, this is significant only on the initial application. On repeated sequential applications, the residual drug in the application site of the patch is absorbed by the body at approximately the same rate that drug from the new patch is absorbed into the new application area. Thus the patient should not experience any interruption of the therapeutic effect, such as analgesia. When the patch is removed, the therapeutic effect continues until the amount of residual drug in the skin is reduced and the drug cleared from the systemic circulation via various metabolic pathways.

When continuous therapeutic effect is desired the used patch would be removed and a fresh patch is applied to a new location. For example, the used patch would be sequentially removed and replaced with a fresh patch at the end of the administration period to provide continual therapeutic effect. Since absorption of the drug from the fresh patch into the new application area usually occurs at substantially the same rate as absorption by the body of the residual drug within the previous application site of the patch, blood levels will remain substantially constant.

Depending on the drug to be delivered, administration of a patch can be maintained for a few days, e.g., at least three days, and up to 7 days, with 3-4 day regimen being considered preferable. In certain preferred embodiments, at least 3%, but not more than 40%, of the total amount of the drug in the patch is administered during approximately the first 24 hours of use; at least 6%, but not more than 50%, of the total amount of the drug is administered during approximately the first 48 hours of use; and at least 10%, but not more than 75%, of the total amount of the drug is administered during the administration period.

Methods of Manufacture

The transdermal devices are manufactured according to known methodology. For example, in an embodiment, a solution of the polymeric reservoir material, as described above, is added to a double planetary mixer, followed by addition of desired amounts of the drug, permeation enhancers, and other ingredients that may be needed. Preferably, the polymeric reservoir material is an acrylate material. The acrylate material is solubilized in an organic solvent, e.g., ethanol, ethyl acetate, hexane, and the like. The mixer is then closed and activated for a period of time to achieve acceptable uniformity of the ingredients. The mixer is attached by means of connectors to a suitable casting die located at one end of a casting/film drying line. The mixer is pressurized using nitrogen to feed solution to the casting die. Solution is cast as a wet film onto a moving siliconized polyester web. The web is drawn through the lines and a series of ovens are used to evaporate the casting solvent to acceptable residual limits. The dried reservoir film is then laminated to a selected backing membrane and the laminate is wound onto the take-up rolls. In subsequent operations, individual transdermal patches are die-cut, separated and unit-packaged using suitable pouchstock. Patches are placed in cartons using conventional equipment. In another process, the drug reservoir can be formed using dry-blending and thermal film-forming using equipment known in the art. Preferably, the materials are dry blended and extruded using a slot die followed by calendering to an appropriate thickness.

EXAMPLES

Below are examples of specific embodiments for carrying out the present invention. The examples are offered for illustrative purposes only, and are not intended to limit the scope of the present invention in any way. In the following examples all percentages are by weight unless noted otherwise. $T_g$ was determined by DSC (Differential Scanning calorimetry) with 10° C./min heating rate. Modulus G' is storage modulus at 25° C. and 1 rad/s frequency (Frequency sweep experiment was conducted using AR-2000 rheometer from TA Instruments (TA Instruments, 109 Lukens Drive, New Castle, Del. 19720). The test conditions were: strain 1%, temperature 25° C., frequency range 0.1 to 100 rad/s, gap around 1000 micron). Creep compliance tests were conducted using AR-2000 rheometer from TA Instruments. The test conditions were: stress 1000 dyn/cm$^2$, temperature 30° C., time 3600 seconds, gap around 1000 microns. One skilled in the art will know how to measure $T_g$, creep compliance, and storage modulus in view of the present disclosure.

Transdermal flux can be measured with a standard procedure using Franz cells or using an array of formulations. Flux experiments were done on isolated human cadaver epidermis. With Franz cells, in each Franz diffusion cell a disc of epidermis is placed on the receptor compartment. A transdermal delivery system is placed over the diffusion area (1.98 cm$^2$) in the center of the receptor. The donor compartment is then added and clamped to the assembly. At time 0, receptor medium solution (between 21 and 24 ml, exactly measured) is added into the receptor compartment and the cell maintained at 35° C. This temperature yields a skin surface temperature of 30-32° C. Samples of the receptor compartment are taken periodically to determine the skin flux and analyzed by HPLC. In testing flux with an array of transdermal miniature patches, formulations are prepared by mixing stock solutions of each of the mixture components of formulation in organic solvents (about 15 wt % solids), followed by a mixing process. The mixtures are then aliquoted onto arrays as 4-mm diameter drops and allowed to dry, leaving behind solid samples or "dots." (i.e., mini-patches). The miniature patches in the arrays are then tested individually for skin flux using a permeation array, whose principle of drug flux from a formulation patch through epidermis to a compartment of receptor medium is similar to that of Franz cells (an array of miniature cells). The test array has a plurality of cells, a piece of isolated human epidermis large enough to cover the whole array, and a multiple well plate with wells acting as the receptor compartments filled with receptor medium. The assembled permeation arrays are stored at 32° C. and 60% relative humidity for the duration of the permeation experiments. Receptor fluid is auto-sampled from each of the permeation wells at regular intervals and then measured by HPLC for flux of the drug.

Example 1

A monomer mix containing butyl acrylate, 2-hydroxyethyl acrylate, t-octyl acrylamide, acrylic acid, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The ratios of the monomers and initiator added totally, i.e., butyl acrylate:2-hydroxyethyl acrylate:t-octyl acrylamide:acrylic acid:AIBN were 59:25.5:9.5:6:2. The material was then held at reflux for a suitable period of time. At the end of the hold period, the contents were cooled to room temperature and the solution polymer discharged. The dry film made from this polyacrylate formulation had storage modulus of around $9 \times 10^5$ dyn/cm$^2$, creep compliance of around $7 \times 10^{-5}$ cm$^2$/dyn, and glass transition temperature of $-8°$ C., and consequently was too stiff to provide adequate adhesive properties alone. This formed a proadhesive.

Example 2

A monomer mix containing butyl acrylate, 2-hydroxypropyl acrylate, t-octyl acrylamide, acrylic acid, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The material was held at reflux for a suitable period of time. The ratios of the monomers and initiator added totally, i.e., butyl acrylate:2-hydroxypropyl acrylate:t-octyl acrylamide:acrylic acid:AIBN were 59:25.5:9.5:6:2. At the end of the hold period, the contents were cooled to room temperature and the solution polymer discharged. The dry film made from this polyacrylate formulation had storage modulus of around $8 \times 10^5$ dyn/cm$^2$, creep compliance of around $4 \times 10^5$ cm$^2$/dyn, and glass transition temperature of $-8°$ C., and consequently was too stiff to provide adequate adhesive properties alone. This formed a proadhesive.

Example 3

A monomer mix containing vinyl acetate, 2-hydroxyethyl acrylate, 2-ethylhexyl acrylate, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The material was held at reflux for a suitable period of time. The ratios of the monomers and initiator added totally, i.e., vinyl acetate:2-hydroxyethyl acrylate:2-ethylhexyl acrylate:AIBN were 50:10:40:1.2. At the end of the hold period, the contents were cooled to room temperature and the solution polymer discharged. The dry film made from this polyacrylate formulation had storage modulus of around $2 \times 10^6$ dyn/cm$^2$, creep compliance of around $4 \times 10^{-6}$ cm$^2$/dyn, and glass transition temperature of $-14°$ C., and consequently was too stiff to provide adequate adhesive properties alone. This formed a proadhesive.

Example 4

A monomer mix containing vinyl acetate, 2-hydroxyethyl acrylate, 2-ethylhexyl acrylate, ethyl acetate (solvent), and 2,2'-azobisisobutyronitrile (AIBN) (polymerization initiator) was prepared. A fraction was charged to an appropriate vessel and heated to reflux with stirring. The remainder was added to the vessel over time. The ratios of the monomers and initiator added totally, i.e., vinyl acetate:2-hydroxyethyl acrylate:2-ethylhexyl acrylate:AIBN were 60:20:20:1.2. The material was held at reflux for a suitable period of time. At the end of the hold period, the contents were cooled to room temperature and the solution polymer discharged. The dry film made from this polyacrylate formulation had storage modulus of around $4 \times 10^6$ dyn/cm$^2$, creep compliance of around $2 \times 10$ cm$^2$/dyn, and glass transition temperature of $-8°$ C., and consequently was too stiff to provide adequate adhesive properties alone. This formed a proadhesive.

Example 5

Polyacrylate adhesive DURO-TAK® 87-2287, (from National Starch &. Chemical Co.) and proadhesives from EXAMPLE 3 and EXAMPLE 4 were analyzed with and without permeation enhancers. The data in Table 1 clearly demonstrate the effect of enhancer on the properties of current commercial acrylic adhesive as well as the novel polyacrylate compositions described in this application. DURO-TAK® 87-2287 adhesive with a $T_g$ of $-34°$ C. had severe cold flow at 20% lauryl lactate loading level. (The monomeric components of DURO-TAK® 87-2287 are mostly vinyl acetate, 2-ethylhexyl acrylate, and hydroxyethyl acrylate.) Such cold flow phenomenon is the reason this adhesive and most similar commercial pressure sensitive adhesive systems are not suitable for applications where relatively high loadings of enhancers are needed. LL is enhancer lauryl lactate. DURO-TAK® 87-2287 had unacceptable rheological properties (severe cold flow) for transdermal application in the presence of 20% lauryl lactate. (Based on this invention, it was also found that many other PSA's with $T_g$, creep compliance and storage modulus similar to DURO-TAK® 87-2287 in the range suitable for PSA as is would behave similarly). The data in Table 1 demonstrated that the current commercial acrylate PSA were not suitable for applications where high loading of enhancers is needed. It was found that transdermal patches started to have undesirable rheological properties, such as the tendency to cold flow and low cohesive strength, when creep compliance is larger than $6 \times 10$ cm$^2$/dyn. It has been found that typically for the prior commercial transdermal PSAs, enhancer loading is usually less than 20% due to the impact of enhancer on PSA rheological properties.

The improvement of enhancer tolerance using the novel polyacrylate composition described in this application can also be seen from the data in Table 1. By increasing the ratio of hard to soft monomer in the formulation, the glass transition temperatures were increased. The molecular weight was also increased. As a result, the polyacrylate compositions described in EXAMPLES 3 and 4 had higher modulus and lower creep compliance as can be seen from the data in Table 1. This resulted in polyacrylate compositions not suitable for pressure sensitive adhesive application in pure form due to high modulus. However, these polyacrylate compositions had better enhancer tolerance. As a result, the compositions after the addition of 35 wt % LL had the desired rheological properties for transdermal application. As can be seen from the data in Table 1, desirable creep compliance was still present when enhancer loading was 35 wt %.

Further, the data in Table 2 showed that when compared to another currently available commercial pressure sensitive adhesive DURO-TAK® 87-4287, the polyacrelate from Example 3 provides better enhancer tolerance.

TABLE 1

Effect of enhancer lauryl lactate (LL) on adhesive properties.

| Sample | $T_g$, °C. | Modulus G', dyn/cm$^2$ | Creep compliance, cm$^2$/dyn |
|---|---|---|---|
| DURO-TAK ® 87-2287 | −34 | $2.1 \times 10^5$ | $1.3 \times 10^{-4}$ |
| Polyacrylate composition from EXAMPLE 3 | −14 | $2.0 \times 10^6$ | $4.0 \times 10^{-6}$ |
| Polyacrylate composition from EXAMPLE 4 | −8 | $4.0 \times 10^6$ | $2.0 \times 10^{-6}$ |
| 20 wt % LL in DURO-TAK ® 87-2287 | — | $5.6 \times 10^4$ | $1.84 \times 10^{-3}$ |
| 34 wt % LL in Polyacrylate composition from EXAMPLE 3 | — | $1.0 \times 10^5$ | $3.2 \times 10^{-4}$ |
| 35 wt % LL in Polyacrylate composition from EXAMPLE 4 | — | $1.2 \times 10^5$ | $4.0 \times 10^{-4}$ |

TABLE 2

Effect of enhancer oleic acid (OA) on adhesive properties.

| Sample | $T_g$, °C. | Modulus G', dyn/cm$^2$ | Creep compliance, cm$^2$/dyn |
|---|---|---|---|
| DURO-TAK ® 87-4287 | −34 | $3.4 \times 10^5$ | $4.3 \times 10^{-5}$ |
| Polyacrylate composition from EXAMPLE 3 | −14 | $2.0 \times 10^6$ | $4.0 \times 10^{-6}$ |
| 25 wt % OA in DURO-TAK ® 87-4287 | — | $4.9 \times 10^4$ | $9.1 \times 10^{-4}$ |
| 35 wt % OA in Polyarylate composition from EXAMPLE 3 | — | $6.1 \times 10^4$ | $2.0 \times 10^{-4}$ |

Specific examples of various transdermal patches of the invention that are capable of administering drugs for extended periods of time will be described in the examples below. The adhesive-reservoir patches in which the reservoir includes a single phase polymeric composition of free undissolved components containing an therapeutically effective amount of drug at subsaturation concentration are preferred.

Example 6

A transdermal patch containing active substance galantamine were prepared as follows:
91.6 g polyacrylate solution (a 34.53 wt % solution of the polyacrylate described in EXAMPLE 1), 13.5 g galantamine, 3.0 g lauric acid, 2.3 g lauryl pyrrolidone, and 4.6 g oleic acid were mixed and homogenized. The solution was spread at a thickness of 12-15 mil (0.3-0.375 mm) on a siliconized PET film that is about 2-3 mil (0.05-0.075 mm) thick. The mass was dried at 65° C. over a period of 90 minutes. After solvent evaporation, a 2-3 mil (0.05-0.075 mm) thick PET backing layer was laminated on to the adhesive drug reservoir layer using standard procedures. Individual patches with different size were die-cut from this laminate. It was found that the polyacrylate adhesive in the resulting patch had desirable storage modulus of around $2.1 \times 10^5$ dyn/cm$^2$, and desirable creep compliance of around $4.1 \times 10^{-4}$ cm$^2$/dyn. Comparatively, the polyacrylate without the drug and the enhancers had glass transition temperature of −8° C., storage modulus of around $9 \times 10^5$ dyn/cm$^2$, and creep compliance of around $7 \times 10^{-5}$ cm$^2$/dyn, and was too stiff and had inadequate adhesive properties. It was found that the patches could deliver galantamine through cadaver skin in a Franz cell at a flux rate of 8.9 µg/cm$^2$·hr. This shows such polyacrylate can be made into patches for galantamine therapy, e.g., for dementia, Alzheimer disease, etc.

Example 7

A 99.8 g polyacrylate solution (about 36.92 wt % of polyacrylate described in EXAMPLE 2), 15.6 g galantamine, 12.1 g oleic acid, and 1.0 g lauric acid were mixed and homogenized. The resulting solution was spread at a thickness of 10-12 mil on a silicone-coated PET film about 2-3 mil (0.05-0.075 mm) thick. The mass was dried at 65° C. over a period of 90 minutes. After solvent evaporation, a 2-3 mil (0.05-0.075 mm) thick PET backing layer was laminated on to the adhesive drug reservoir layer using standard procedures. Individual patches with different size were die-cut from this laminate. It was found that the polyacrylate adhesive in the resulting patch had desirable storage modulus of around $3.2 \times 10^5$ dyn/cm$^2$, and desirable creep compliance of around $2.2 \times 10^{-4}$ cm$^2$/dyn. Comparatively, the polyacrylate without the drug and the enhancers had glass transition temperature of −8° C., storage modulus of around $9 \times 10^5$ dyn/cm$^2$ and creep compliance of around $7 \times 10^{-5}$ cm$^2$/dyn, and was too stiff and had inadequate adhesive properties. It was found that the patches can deliver galantamine through cadaver skin in a Franz cell at a flux rate of 10.9 µg/cm$^2$·hr. This shows such polyacrylate can be made into patches for galantamine therapy, e.g., for dementia, Alzheimer disease, etc.

Example 8

A transdermal patch containing active substance norelgestromin were prepared as follows:
A 100.0 g polyacrylate solution (about 42.9 wt % of polyacrylate described in EXAMPLE 3), 3.6 g norelgestromin, 7.8 g GMO, and 1.7 g NLS were mixed and homogenized. The resulting solution was spread at a thickness of 10-12 mil on a silicone-coated PET film of about 2-3 mil (0.05-0.075 mm) thickness. The mass was dried at 65° C. over a period of 90 minutes. After solvent evaporation, a 2-3 mil (0.05-0.075 mm) thick PET backing layer was laminated on to the adhesive drug reservoir layer using standard procedures. Individual patches with different size were die-cut from this laminate. It was found that the polyacrylate adhesive in the resulting patch had desirable storage modulus of around $3.1 \times 10^5$ dyn/cm$^2$ and desirable creep compliance of around $6.2 \times 10^{-5}$ cm$^2$/dyn. Comparatively, the polyacrylate without the drug and the enhancers had a storage modulus of around $4 \times 10^6$ dyn/cm$^2$ and a creep compliance of around $2 \times 10^{-6}$ cm$^2$/dyn and was too stiff and had inadequate adhesive properties. Further, it has been shown that the polyacrylate of EXAMPLE 3 after incorporating a large amount of permeation enhancer into a single phase (see Table 1), although without the drug, had adequate PSA properties. It was found that the patches were able to deliver norelgestromin through cadaver skin in a Franz cell at a flux rate of 0.4 µg/cm$^2$·hr. This shows such polyacrylate can be made into patches for norelgestromin therapy, e.g., for hormone replacement, birth control, etc.

Example 9

Nicotine hexanoate (200 grams) is added to 10 Kg of a solution of the polyacrylate of Example 2 (from National Starch & Chemicals, Bridgewater, N.J.) in a blended solvent mixture of isopropyl alcohol (13 wt %) and 87 wt % ethyl acetate to result in a 20 wt % solids in solvent(s) solution. This polyacrylate is a polar copolymer and consisted of 26 wt % hydroxyl monomer, 6 wt % monomer with carboxylic acid groups, t-octyl acrylamide, and butyl acrylate. The solution is mixed well and was transferred to a pressurized casting vessel. This solution is fed to a casting head set up to lay down a 0.25 mm wet thickness film onto a moving web of siliconized polyester, 0.075 mm thick. The film is moved at a rate of about 5 feet per minute through a series of three ovens 30 feet long. The ovens are set at 45 degrees ° C., 85° C. and 95° C., with a total residence time of six minutes. After exiting the ovens, the films would contain typically less than 500 ppm of residual solvent(s). After exiting the ovens, a transdermal backing is laminated to the reverse side of the polyacrylate adhesive. The backing was a 0.05 mm thick layer of linear low density polyethylene. Individual systems of about 3 cm² are cut and the flux of which is tested. It is expected that they have acceptable flux and that such polyacrylate can be made into patches for nicotine therapy, e.g., for smoking cessation.

The practice of the present invention will employ, unless otherwise indicated, conventional methods used by those in pharmaceutical product development within those of skill of the art. Embodiments of the present invention have been described with specificity. The embodiments are intended to be illustrative in all respects, rather than restrictive, of the present invention. It is to be understood that various combinations and permutations of various parts and components of the schemes disclosed herein can be implemented by one skilled in the art without departing from the scope of the present invention. Further, where a substance is described to comprise certain ingredients, it is contemplated that a substance also be made consisting essentially of the ingredients.

What is claimed is:

1. A method for transdermal administration of a drug, comprising:
   providing a transdermal drug delivery device, the device comprising an adhesive reservoir including at least one drug, at least one permeation enhancer, and an acrylate polymer, wherein the at least one drug and the at least one permeation enhancer are dissolved in a combined amount of at least 30 wt % in the acrylate polymer, and the acrylate polymer has a $T_g$ of greater than $-10°$ C. without the at least one permeation enhancer and without the at least one drug, the acrylate polymer comprising a soft monomer component of no more than 40 wt %, 40 wt % or more of a hard monomer component, at least a portion of the hard monomer component being hard polar functional monomer, and 10 to 35 wt % of a polar functional monomer component, at least a portion of the polar functional monomer component being hard polar functional monomer; and
   applying the device to a body surface of an individual.

2. The method of claim 1, wherein the acrylate polymer used in forming the reservoir is of a composition having a creep compliance of $6 \times 10^{-5}$ cm²/dyn to $2 \times 10^{-6}$ cm²/dyn without the at least one drug and without the at least one permeation enhancer.

3. The method of claim 1, wherein the acrylate polymer includes at least one of a functional monomer with a hydroxyl group and a functional monomer with a carboxylic acid group.

4. The method of claim 1, wherein the acrylate polymer includes an acrylic copolymer resulting from (i) a soft alkyl acrylate monomer component, in which each soft alkyl acrylate monomer has a homopolymer $T_g$ of $-80$ to $-20°$ C. and (ii) 40 to 60 wt % of a nonfunctional hard modifying monomer component, in which each hard modifying monomer has a homopolymer $T_g$ of 0 to 250° C.

5. The method of claim 1, wherein the acrylate polymer has (i) a soft alkyl acrylate monomer component, in which each soft alkyl acrylate monomer has a homopolymer $T_g$ of $-80$ to $-20°$ C. and (ii) 40 to 60 wt % of a nonfunctional hard modifying monomer component, in which each hard modifying monomer has a homopolymer $T_g$ of 0 to 250° C.

6. The method of claim 1, wherein the soft monomer component comprises a soft acrylate monomer selected from the group consisting of butyl, hexyl, 2-ethylhexyl, octyl, and dodecyl acrylates and isomers thereof.

7. The method of claim 1, wherein the acrylate polymer includes a soft alkyl acrylate monomer component having a homopolymer $T_g$ of less than $-20°$ C.

8. The method of claim 1, wherein the acrylate polymer includes a soft alkyl acrylate monomer component having a homopolymer $T_g$ of less than $-20°$ C., a hard modifying monomer having a homopolymer $T_g$ of higher than 20° C., and a functional monomer having an acidic group.

9. The method of claim 1, wherein the acrylate polymer includes a hard modifying monomer having a homopolymer $T_g$ of 0 to 250° C., wherein the at least one permeation enhancer and the at least one drug are dissolved in the acrylate polymer and the acrylate polymer has a $T_g$ of 0 to $-10°$ C. and a creep compliance of $6 \times 10^{-5}$ cm²/dyn to $2 \times 10^{-6}$ cm²/dyn if without the dissolved drug and permeation enhancer, whereas the adhesive reservoir with the dissolved drug and permeation enhancer has a creep compliance of less than $1 \times 10^{-3}$ cm²/dyn and a storage modulus of $1 \times 10^5$ dyn/cm² to $8 \times 10^5$ dyn/cm².

10. The method of claim 1, wherein the acrylate polymer includes hard modifying monomer having a homopolymer $T_g$ of 40 to 100° C.

11. The method of claim 1, wherein the acrylate polymer includes hard modifying monomer selected from the group consisting of vinyl acetate, methyl acrylate, and methyl methacrylate.

12. The method of claim 1, wherein the acrylate polymer has an acidic group and a hydroxyl group therein and includes 5 to 15 wt % of a nonfunctional hard monomer component.

13. The method of claim 1, wherein the acrylate polymer has monomer components consisting essentially of 50 to 60 wt % vinyl acetate, 10-20 wt % hydroxyethyl acrylate, and 20-40 wt % 2-ethylhexyl acrylate.

14. The method of claim 1, wherein the acrylate polymer includes functional monomer selected from the group consisting of acrylic acid, hydroxyethyl acrylate, and hydroxypropyl acrylate.

15. The method of claim 1, wherein the at least one permeation enhancer and the at least one drug are dissolved in the acrylate polymer and the acrylate polymer has a $T_g$ of 0 to $-10°$ C., and a creep compliance of $6 \times 10^{-5}$ cm²/dyn to $2 \times 10^{-6}$ cm²/dyn if without the dissolved drug and permeation enhancer, whereas the acrylate polymer with the drug and permeation enhancer dissolved therein forms an adhesive reservoir with a $T_g$ of $-10$ to $-20°$ C., a creep compliance of less than $1 \times 10^{-3}$ cm²/dyn and a storage modulus of $1 \times 10^5$ dyn/cm² to $8 \times 10^5$ dyn/cm².

16. The method of claim 1, wherein the acrylate polymer has a $T_g$ of 0 to $-10°$ C. if without drug and permeation enhancer, whereas the acrylate polymer having drug and permeation enhancer at above 30 wt % in a single phase forms an adhesive reservoir with a $T_g$ of $-10$ to $-20°$ C., a creep compliance of $1 \times 10^{-4}$ cm²/dyn to $6 \times 10^{-4}$ cm²/dyn, and a storage modulus of $1 \times 10^5$ dyn/cm² to $8 \times 10^5$ dyn/cm².

17. The method of claim 1, wherein the acrylate polymer has a $T_g$ of 0 to $-10°$ C., storage modulus of $8 \times 10^5$ dyn/cm² or above if without drug and permeation enhancer, whereas the acrylate polymer with drug and permeation enhancer at above 30 wt % dissolved therein forms an adhesive reservoir with a $T_g$ of $-10$ to $-40°$ C., a creep compliance of $1 \times 10^{-4}$ cm²/dyn to $6 \times 10^{-4}$ cm²/dyn, and storage modulus of $1 \times 10^5$ dyn/cm² to $8 \times 10^5$ dyn/cm².

18. The method of claim 1, wherein the at least one drug is a basic drug.

19. The method of claim 1, wherein the at least one drug is selected from the group consisting of fentanyl, fentanyl analog, galantamine, and norelgestromin.

20. A method for transdermal administration of a drug, the method comprising:

provinding a transdermal drug delivery device, the device comprising an adhesive reservoir including at least one drug and at least one permeation enhancer dissolved in an acrylate polymer, the acrylate polymer having a $T_g$ of 0 to $-10°$ C., a creep compliance of below $7 \times 10^{-5}$ cm$^2$/dyn, and a storage modulus of $8 \times 10^5$ dyn/cm$^2$ or above without the at least one drug and the at least one permeation enhancer, wherein the acrylate polymer constitutes 50 wt % to 70 wt % of the reservoir and is capable of holding the at least one drug and the at least one permeation enhancer combination at a dissolved amount of at least 30 wt %, wherein the adhesive reservoir having dissolved therein the at least one drug and the at least one permeation enhancer in an amount of at least 30 wt % has a $T_g$ of $-10$ to $-40°$ C., a creep compliance of $1 \times 10^{-4}$ cm$^2$/dyn to $6 \times 10^{-4}$ cm$^2$/dyn and storage modulus of $1.2 \times 10^5$ dyn/cm$^2$ to $6 \times 10^5$ dyn/cm$^2$, the acrylate polymer including a soft monomer alkyl acrylate component, a hard monomer selected from the group consisting of acrylic acid, methyl acrylate, vinyl acetate, and methyl methacrylate and a functional monomer component including at least one of a carboxyl group and a hydroxyl group; and applying the device to a body surface of an individual.

\* \* \* \* \*